United States Patent
Rieger et al.

(10) Patent No.: US 10,562,025 B2
(45) Date of Patent: Feb. 18, 2020

(54) CYTOMETER UNIT COMPRISING DUAL FIXING DEVICES, CYTOMETRIC METHOD, ROTATABLE SAMPLE CARRIER AND CORRESPONDING USE THEREOF

(71) Applicant: Testo SE & CO. KGaA, Lenzkirch (DE)

(72) Inventors: Robert Rieger, Freiburg (DE); Philipp Von Olshausen, Freiburg (DE); Martin Strnad, Glotteral (DE)

(73) Assignee: Testo SE & Co. KGaA, Lenzkirch (DE)

( * ) Notice: Subject to any disclaimer, the term of this patent is extended or adjusted under 35 U.S.C. 154(b) by 174 days.

(21) Appl. No.: 15/566,033

(22) PCT Filed: Apr. 12, 2016

(86) PCT No.: PCT/EP2016/000602
§ 371 (c)(1),
(2) Date: Oct. 12, 2017

(87) PCT Pub. No.: WO2016/169641
PCT Pub. Date: Oct. 27, 2016

(65) Prior Publication Data
US 2018/0111120 A1 Apr. 26, 2018

(30) Foreign Application Priority Data
Apr. 22, 2015 (DE) .......... 10 2015 005 134

(51) Int. Cl.
*G01N 15/14* (2006.01)
*B01L 3/00* (2006.01)
(Continued)

(52) U.S. Cl.
CPC ... *B01L 3/502715* (2013.01); *B01L 3/502761* (2013.01); *G01N 15/1434* (2013.01);
(Continued)

(58) Field of Classification Search
CPC .......... G01N 15/1434; G01N 15/1006; G01N 2015/1452; G01N 33/54313;
(Continued)

(56) References Cited

U.S. PATENT DOCUMENTS

| | | | |
|---|---|---|---|
| 4,609,991 A | * | 9/1986 | Minton ............... G01N 15/04 356/246 |
| 8,242,433 B2 | * | 8/2012 | Kim ............... B01L 3/502715 250/231.13 |

FOREIGN PATENT DOCUMENTS

| | | |
|---|---|---|
| EP | 2072134 | 6/2009 |
| EP | 2237045 | 10/2010 |
| WO | 2016050750 | 4/2016 |

* cited by examiner

*Primary Examiner* — Que Tan Le
(74) *Attorney, Agent, or Firm* — Volpe and Koenig, P.C.

(57) ABSTRACT

In a cytometer unit (1) with a receptacle (2) into which a rotatable and preferably disk-shaped sample carrier (3) is insertable, it is proposed to define a first fixing means (14) for the definition of a position of a cytometer channel (12) of the inserted sample carrier (3) transversely with respect to the direction of extent thereof and transversely with respect to an optical path (11), by which a cytometric measurement can be carried out, and to use a second fixing means (19) to define a position of the cytometer channel (12) of the inserted sample carrier (3) along the optical path (11).

16 Claims, 6 Drawing Sheets

(51) Int. Cl.
 *G01N 15/04* (2006.01)
 *G01N 15/10* (2006.01)
(52) U.S. Cl.
 CPC . *B01L 2200/025* (2013.01); *B01L 2300/0803* (2013.01); *B01L 2400/0409* (2013.01); *G01N 2015/045* (2013.01); *G01N 2015/1006* (2013.01); *G01N 2015/1452* (2013.01)
(58) Field of Classification Search
 CPC ............. B01L 3/0293; B01L 3/502715; B01L 2200/025; B01L 3/502761
 USPC .............................. 250/221, 222.2, 573, 576
 See application file for complete search history.

CYTOMETER UNIT COMPRISING DUAL FIXING DEVICES, CYTOMETRIC METHOD, ROTATABLE SAMPLE CARRIER AND CORRESPONDING USE THEREOF

BACKGROUND

The invention relates to a cytometer unit with a receptacle for an insertable, rotatable and preferably disk-shaped sample carrier, wherein a rotation unit which can be coupled to an inserted sample carrier, and with which the sample carrier inserted into the receptacle is rotatable, is arranged in the receptacle, and wherein an optical path for carrying out a cytometric measurement on a cytometer channel of the inserted sample carrier is formed in the receptacle.

Cytometer units of this kind are known and are used to carry out cytometric tests in semi-automated or fully automated methods. The disk-shaped sample carrier can in this case be designed as a disposable article, as a result of which it is possible to dispense with complicated cleaning steps prior to carrying out the test method again.

It has been found that the measurement accuracy of the cytometric test method may be sensitive to and depend on the optical path being precisely oriented with respect to the cytometer channel. The optical path often has a non-uniform cross section along its course, and it is particularly desirable to bring the cytometer channel into a focusing portion of the optical path.

The invention further relates to a cytometry method in which, for a cytometric measurement, a cytometer channel formed in a sample carrier and containing a sample to be tested is brought into an optical path.

The invention moreover relates to a rotatable and preferably disk-shaped sample carrier with a cytometer channel and with a coupling site for a rotation unit.

The invention relates finally to a use of a rotatable and preferably disk-shaped sample carrier, in particular as described above, with a preferably radially oriented cytometer channel and with a coupling site for a rotation unit.

SUMMARY

The object of the invention is to simplify the orientation of a cytometer channel of a sample carrier relative to an optical path of a cytometer unit.

According to the invention, the stated object is achieved by one or more features of the invention. In particular, the stated object is thus achieved according to the invention, in a cytometer unit of the type described at the outset, by the fact that a first fixing means is formed with which the inserted sample carrier can be contacted and a position of the cytometer channel can thus be defined in a first adjustment direction transversely with respect to the optical path, and by the fact that a second fixing means is formed with which the inserted sample carrier can be contacted and a position of the cytometer channel can thus be defined in a second adjustment direction along the optical path in a position contacting the inserted sample carrier. It is advantageous that fixing means for orientation of the sample carrier in a two-step method after its insertion into the receptacle are configured such that automated orientation can be achieved. It is thus possible to avoid complicated manual adjustment steps. The orientation of the cytometer channel in preparation for the cytometric test in a cytometry method can thus be made easier.

It is generally advantageous if the interaction between the first fixing means and the sample carrier is configured to permit an automatic and/or machine—processable orientation of the sample carrier in the first adjustment direction. For example, this can be configured by a mechanical interaction, in particular a form-fit engagement. In further embodiments, a machine-processable interaction, for example an electrical, optical and/or magnetic interaction, can be set up additionally or alternatively.

A rotatable sample carrier is generally suitable for carrying out a centrifuging step. It is particularly expedient if the sample carrier is disk-shaped, i.e. if it has a third dimension that is considerably smaller than the other two dimensions. This has the advantage that the material utilization in particular for receiving two-dimensional microfluid structures is particularly expedient.

In one embodiment of the invention, provision can be made that the first fixing means contacts the sample carrier on one side. In this way, a simplified structural set-up and a simplified insertion of the sample carrier into the receptacle can be achieved.

Alternatively or in addition, provision can be made that the second fixing means contacts the sample carrier on one side. In this way too, simplified insertion and simplified orientation can be achieved.

It is particularly expedient if the first fixing means and/or the second fixing means contact(s) the sample carrier in each case axially. It is advantageous that, on the disk-shaped sample carrier, large side surfaces can be utilized to define reference planes or reference lines or reference points. It is particularly expedient if the first fixing means and the second fixing means contact the sample carrier from a common side. In this way, it is possible to ensure that the fixing means do not impede the insertion of the sample carrier.

It can additionally be provided that a holding-down device is designed to contact the inserted sample carrier from a side facing away from the first fixing means and/or the second fixing means. It is advantageous that a positioning of the holding-down device is not necessary for the defined orientation of the cytometer channel with respect to the optical path, and instead a holding-down device can also be used which provides merely a holding function of the oriented sample carrier. It is particularly expedient if the holding-down device is arranged in the continuation or alignment of the optical path. It is in this way possible to achieve a particularly well-defined bearing of the sample carrier on the fixing means.

For example, provision can be made that the first fixing means and/or the second fixing means are/is designed as in each case at least one ball pin. A ball pin can be characterized here, for example, by the fact that a ball or a half ball is arranged on a free end of a pin. It is advantageous that reduced friction arises at the free end of the ball pin and/or that a ball pin makes available a defined bearing point. Both situations are advantageous in respect of a defined and simple orientation of the sample carrier on the fixing means.

For fixing and orientation in the first adjustment direction, provision can be made that the first fixing means interacts with form-fit engagement with a counterpart fixing means on the sample carrier, in particular in order to form a ball latch. By latching into the form-fit, it is easily discernible that an orientation on the first fixing means in the first adjustment direction is achieved. It is thus possible to proceed easily with the orientation in the second adjustment direction.

In one embodiment of the invention, provision can be made that the optical path is formed between at least one part of the first fixing means, in particular a bearing point, and at least one part of the second fixing means, in particular a bearing point. It is thus possible to ensure that an orientation of the cytometer channel with respect to the optical path is defined substantially or completely by the position of the fixing means in space, wherein additional bearing points of the sample carrier, for example on the coupled rotation unit, have little or no effect on the quality of the cytometric test. Thus, in particular, bearing plays, which are necessarily present in rotation units, are acceptable in the orientation of the sample carrier, since an influence of these bearing plays on the quality or precision of the orientation of the cytometer channel on the optical path is avoidable.

It is particularly expedient if the first fixing means and/or the second fixing means, for the definition of the position in the second adjustment direction, form(s) two bearing points for the insertable sample carrier. It is advantageous that an orientation of the sample carrier in the second adjustment direction can be predefined particularly accurately. Provision is preferably made that the two bearing points are formed by the second fixing means. Preferably, one of the bearing points is the bearing point already mentioned regarding the second fixing means. The bearing points of the second fixing means can be spaced apart from each other and can particularly preferably enclose the optical path between them.

It is particularly expedient if the optical path intersects a connection line between the two bearing points. It is thus possible to ensure that a change of a third bearing point of the sample carrier, which can be given for example by the already mentioned rotation unit, only leads to a tilting of the sample carrier about the connection line. By arranging and orienting the optical path in such a way that the optical path intersects the connection line, such tilting about the connection line does not lead to a change of the point of intersection of the optical part with the connection line. If the optical path is now focused on the connection line, a sensitive region for the cytometric measurement is independent of a play of the rotation unit.

Alternatively or in addition, provision can be made that the first fixing means is designed to yield elastically in a direction along the optical path. It is advantageous here that influencing of an orientation or adjustment in the second adjustment direction by the first fixing means can be lessened or even avoided. Provision can be made here that the fixing means is resiliently flexible.

In one embodiment of the invention, provision can be made that the first adjustment direction, with respect to a rotation axis of the rotation unit, is oriented transversely to a radial direction. It is advantageous here that an orientation by change of position of the cytometer channel in the first adjustment direction can be easily carried out by a rotation movement of the rotation unit. Therefore, particularly simple conditions arise when the first adjustment direction is oriented tangentially or in the circumferential direction in relation to the rotation axis of the rotation unit.

Alternatively or in addition, provision can be made that the second adjustment direction, in relation to a rotation axis, for example the already mentioned rotation axis of the rotation unit is oriented transversely with respect to a radial direction, for example the already mentioned radial direction, and a tangential direction. For example, the second adjustment direction can be oriented axially. It is advantageous here that a change of position of the sample carrier or of the cytometer channel in the second adjustment direction cab be effected by an axial displacement of the inserted sample carrier. Axial displacements of this kind can be easily performed, for example, by lowering the sample carrier.

The stated object is alternatively or additionally achieved by the features of the independent claim directed to a cytometry method. According to the invention, in a cytometry method of the type described at the outset, it is thus proposed in particular that the sample carrier is mounted rotatably about a rotation axis, that the sample carrier is contacted by a first fixing means for an orientation of the cytometer channel on the optical path at a distance from the rotation axis in such a way that a position of the cytometer channel is defined in a first adjustment direction transverse to the optical path, and that the sample carrier is contacted by a second fixing means for an orientation of the cytometer channel on the optical path at a distance from the rotation axis in such a way that a position of the cytometer channel is defined in a second adjustment direction along the optical path. Since the cytometer channel often has a homogeneous cross section at least in its measurement portion, the position of the cytometer channel can be characterized, for example, by the position of the cross section of the cytometer channel in relation to the optical path. The invention ensures that an orientation of the cytometer channel can be carried out in a two-step method, which can be automated, without intervention by a user. In this case, the two steps of the method can also be carried out overlapping each other or at the same time. However, it is particularly expedient if the two steps of the method are carried out in succession, i.e. if an orientation is effected in one adjustment direction and then an orientation is effected in another adjustment direction. It is particularly expedient here if the orientation in the first adjustment direction is carried out first and then the orientation in the second direction is carried out.

The orientation of the sample carrier preferably takes place after centrifuging of the sample carrier.

In one embodiment of the invention, provision can be made that the sample carrier is contacted by the first fixing means and/or the second fixing means on one side. This permits a simple configuration of the receiving space. For example, the contacting can take place axially, such that a large surface of the rotatable and preferably disk-shaped sample carrier can be utilized. It is particularly expedient here if the sample carrier is contacted by the first fixing means and the second fixing means from a common side. An automated orientation of the inserted sample carrier can thus be easily performed.

Provision is preferably made that the first fixing means yields during the definition of the position in the second adjustment direction. It is thus possible to avoid a situation where the orientation in the second adjustment direction is impeded by the first fixing means.

In one embodiment of the invention, provision can be made that the first fixing means and a counterpart fixing means of the sample carrier are brought into engagement with each other in order to fix the sample carrier for the definition of the position of the cytometer channel in the first adjustment direction. Form-fit fixing has proven expedient in order to easily ensure and/or easily discern that the oriented position has been reached. Provision can be made here that the counterpart fixing means is a wedge-shaped recess. It is advantageous here that, for example, a ball pin can be easily inserted into the counterpart fixing means in order to obtain an orientation in the first adjustment direction. The fixing means and the counterpart fixing means are preferably brought into engagement with each other as a ball latch.

In one embodiment of the invention, provision can be made that the sample carrier is rotated about the rotation axis for the definition of the position in the first adjustment direction. Thus, the first orientation step can be easily effected with the rotation unit. It is particularly expedient if, before the orientation with the rotation unit, the sample carrier is centrifuged, for example for a sample preparation.

In addition or alternatively, provision can be made that the sample carrier is displaced along the rotation axis for the definition of the position in the second adjustment direction. Thus, an orientation in the second adjustment direction can be effected at least partially by a lowering of the sample carrier in the rotation unit. In addition or alternatively, provision can be made here that, for the definition of the position in the second adjustment direction, the sample carrier is pivoted about a connection line intersecting the optical path. For example, the connection line can extend between two bearing points defined by the first fixing means and/or the second fixing means in the manner already described. It is advantageous that the end position of this pivoting movement does not have to be precisely reached in order to align the optical path with the connection line. Provision is preferably made that a displacement of the sample carrier along the rotation axis is carried out first and that, at the end, a pivoting movement of the sample carrier is carried out in the manner described. The pivoting movement can have a substantially shorter pivot path than the preceding displacement movement. It is advantageous that an orientation in the second adjustment direction can be effected by lowering the sample carrier beyond the bearing points defined by the first fixing means and/or the second fixing means. It can thus rest safely and in a defined manner on the bearing points.

Moreover, in the case of a rotatable and preferably disk-shaped sample carrier of the type described at the outset, the stated object is achieved by the fact that the sample carrier has a counterpart fixing means, wherein the counterpart fixing means is configured for form-fit fixing of the sample carrier transversely with respect to a direction of extent of the cytometer channel. For example, the counterpart fixing means can have a recess of wedge-shape profile, wherein an extent of the wedge shape can be oriented transversely with respect to the extent of the cytometer channel. This can be achieved, for example, by the fact that the counterpart fixing means has a longitudinal extent which is oriented parallel to or along the cytometer channel, for example radially in the case of a radially oriented cytometer channel. The invention thus permits a simplified orientation of the rotatable and preferably disk-shaped sample carrier after insertion into a cytometer unit. Here, the terms radial and axial can be predefined by a coupling site of the sample carrier, with which the sample carrier is coupled to the rotation unit. Thus, the terms radial and axial can also refer, in the position of use, to a rotation axis or rotation unit. The terms radial and axial can thus refer to a rotation axis defined by the rotatability.

Accordingly, the invention proposes a use of a rotatable and preferably disk-shaped sample carrier, in particular as described above and/or according to the claim directed to a rotatable and preferably disk-shaped sample carrier, wherein he disk-shaped sample carrier has a preferably radially oriented cytometer channel, a coupling site for a rotation unit, and a counterpart fixing means, wherein the disk-shaped sample carrier is used in a cytometer unit according to the invention, in particular as described above and/or according to one of the claims directed to a cytometer unit, and/or in a cytometry method according to the invention, in particular as described above and/or according to one of the claims directed to a cytometry method.

The sample carrier is preferably centrifuged prior to the orientation. After the orientation, the cytometric test can take place with the sample carrier stationary.

Accordingly, a preferred use involves a cytometer unit kit with a cytometer unit according to the invention and with an exchangeable rotatable and preferably disk-shaped sample carrier according to the invention.

The invention will now be described in more detail on the basis of illustrative embodiments, but it is not restricted to these illustrative embodiments. Further illustrative embodiments emerge from combination of the features of individual or multiple patent claims with one another and/or with individual or multiple features of the illustrative embodiments.

BRIEF DESCRIPTION OF THE DRAWINGS

The figures used to explain the invention are schematic and very simplified.

DETAILED DESCRIPTION OF THE PREFERRED EMBODIMENTS

FIGS. 1 to 6 are described together in the following.

A cytometer unit according to the invention is designated overall by 1 and has a receptacle 2 into which a rotatable and in this case disk-shaped sample carrier 3 is insertable.

The receptacle 2 formed here by a slit, an extensible tray, a pivotable and/or displaceable cover or generally as an admission opening, can be equipped in a manner known per se with a rotatable, preferably disk-shaped sample carrier 3. The sample carrier 3 is exchangeable and, after use, is replaced by a new sample carrier 3.

Figure 5:
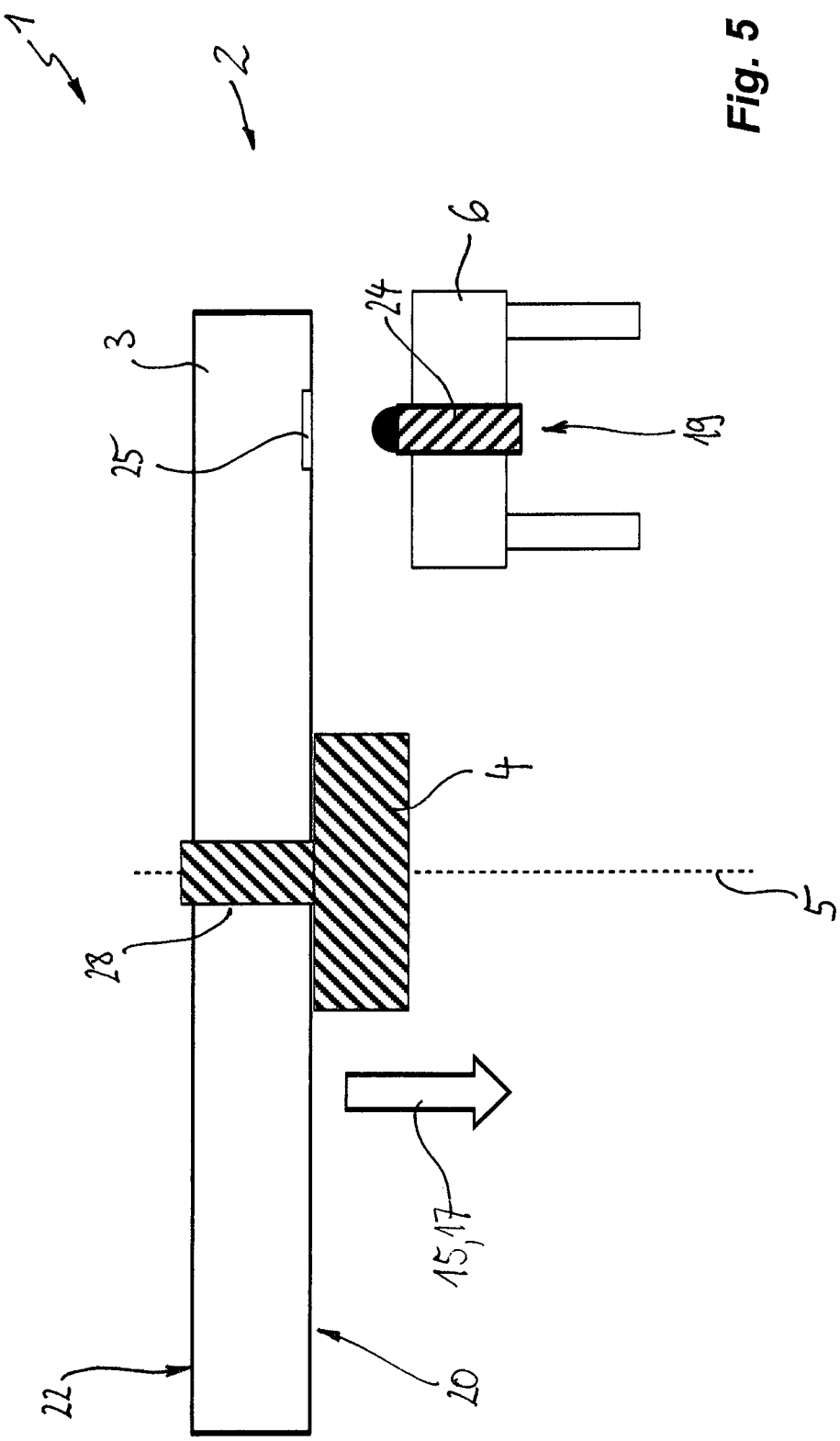
FIG. 5 shows the cytometer unit from FIG. 1 in a sectional view turned through 90° in relation to FIG. 2, during the insertion of the sample carrier.
Figure 6:
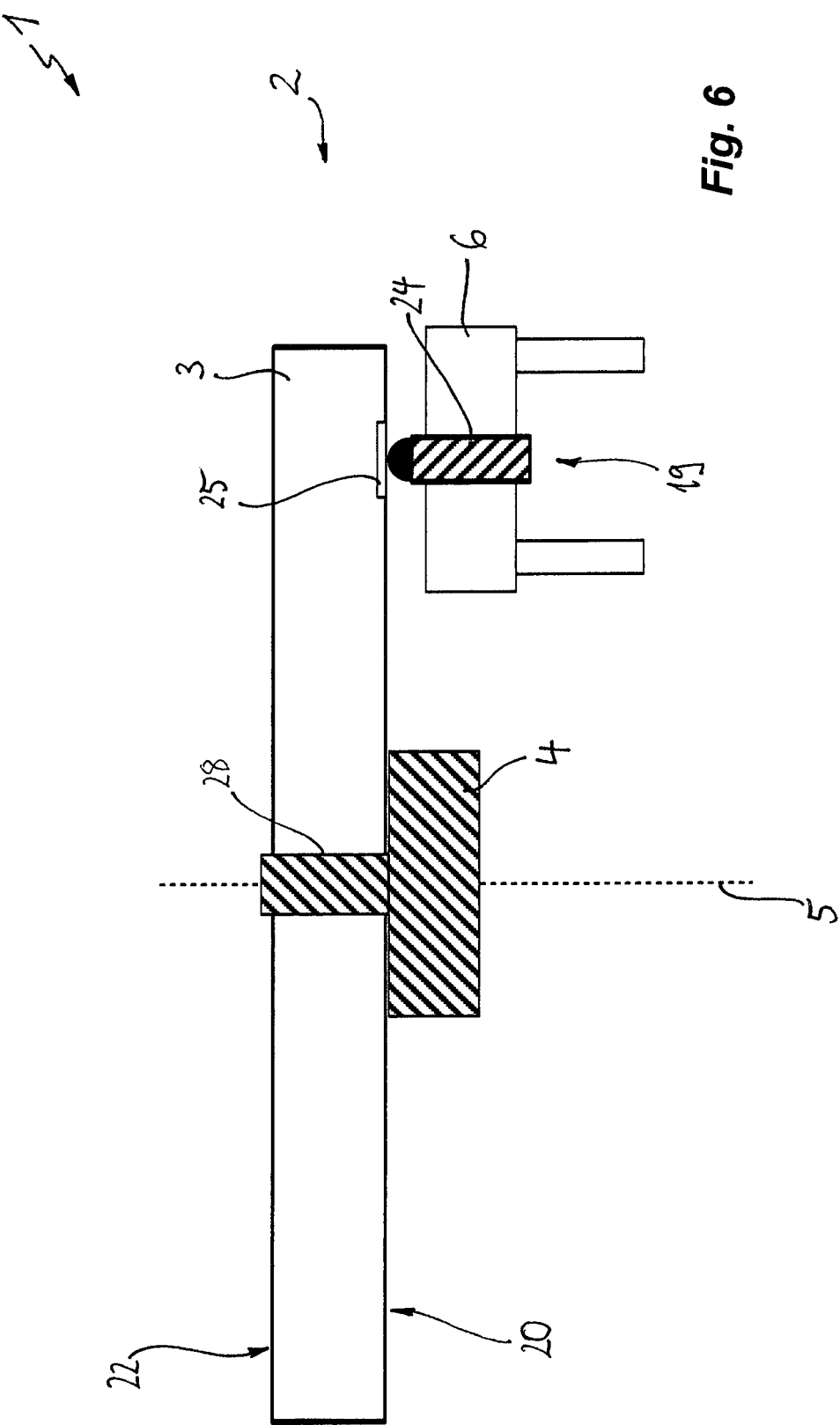
FIG. 6 shows the cytometer unit in a view according to FIG. 5 after the sample carrier has been fixed in the first and the second adjustment direction.

The cytometer unit 1 has a rotation unit 4 indicated in FIG. 5 and FIG. 6, which rotation unit 4 can be coupled to the inserted sample carrier 3. The coupled and inserted sample carrier 3 can be rotated about a rotation axis 5 by the rotation unit 4. The rotation axis 5 can in this case be oriented perpendicularly with respect to a plane predefined by the disk shape of the sample carrier 3. The rotation unit is designed such that an inserted sample carrier 3 coupled to it can be centrifuged.

Figure 2:
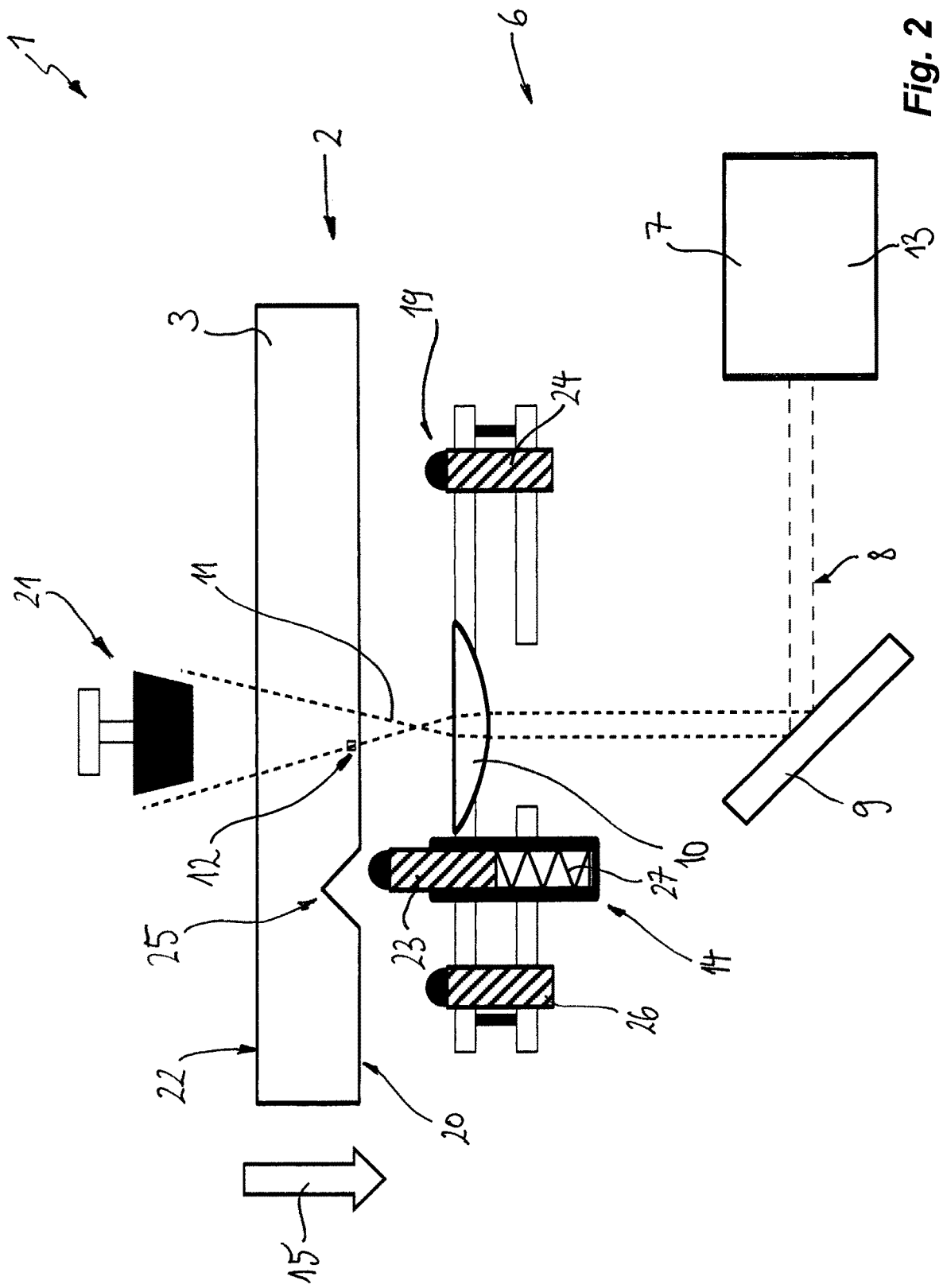
FIG. 2 shows the cytometer unit according to the invention from FIG. 1, in a schematic sectional view before the sample carrier is placed in the position of use for the cytometric measurement.
Figure 3:
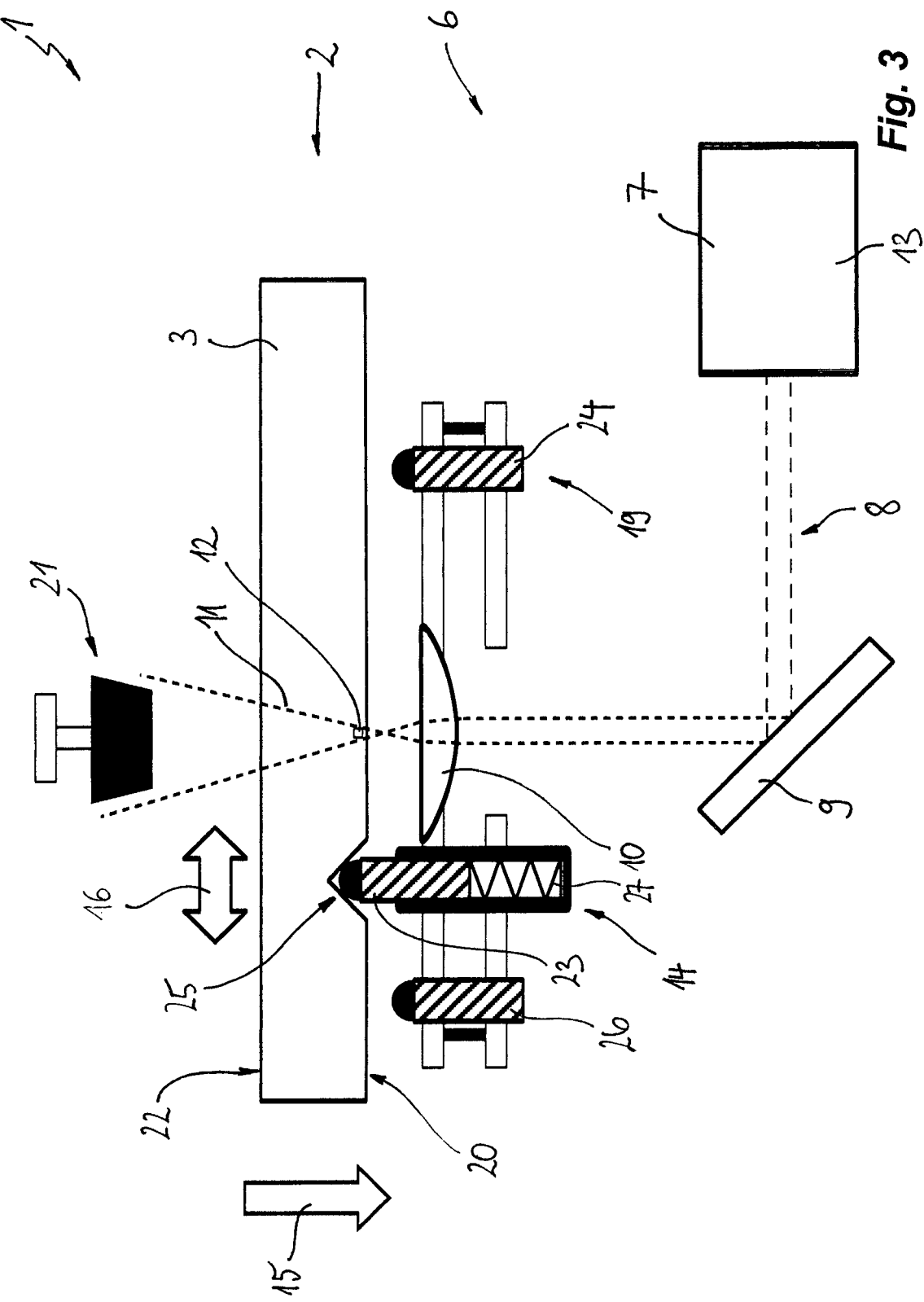
FIG. 3 shows the cytometer unit from FIG. 2 after an adjustment of the inserted sample carrier in a first adjustment direction.
Figure 4:
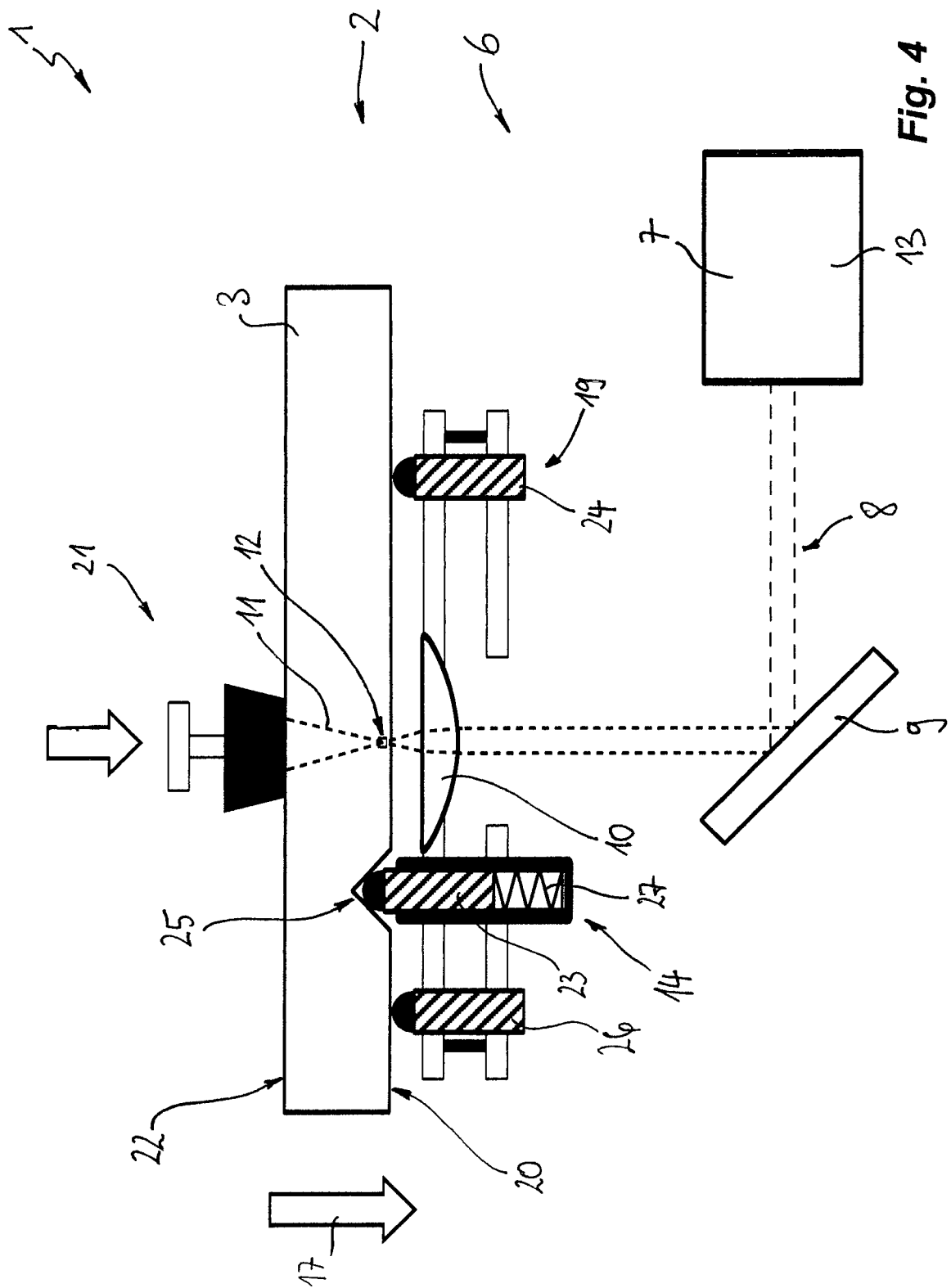
FIG. 4 shows the cytometer unit from FIG. 2 after fixing in a second adjustment direction.

The cytometer unit 1 moreover has an adjusting and measuring unit 6. FIGS. 2 to 4 show the basic internal structure of the adjusting and measuring unit 6. A laser light source 7 serves to generate a light beam 8, which is delivered to the receptacle 2 via at least one mirror 9 and at least one lens 10 of a lens arrangement. The at least one mirror 9 and the at least one lens 10 of the lens arrangement thus define an optical path 11 in the receptacle 2.

The sample carrier 3 has a cytometer channel 12 through which a sample to be tested can flow.

The optical path 11 is designed for carrying out a cytometric measurement on this cytometer channel 12 by means of the fact that the at least one lens 10 of the lens arrangement with the at least one mirror 9 conveys light, which is excited by the light beam 8 in the cytometer channel 12, onto a detector 13, where it is detected.

To carry out this cytometric measurement, the sample carrier 3 is therefore inserted into the receptacle 2. The inserted sample carrier 3 must be oriented with its cytometer channel 12 on the optical path 11. Beforehand, the sample carrier 3 can be centrifuged with the rotation unit 4.

For this orientation, the adjusting and measuring unit 6 has a first fixing means 14, which is shown in FIGS. 1 to 4 and which, for reasons of simplification, has been omitted in FIG. 5 and FIG. 6.

In a manner to be described in further detail, this first fixing means 14 interacts with the sample carrier 3 in such a way that a position of the cytometer channel 12 is defined in a first adjustment direction 16 (cf. FIG. 3). Firstly, by a rotation movement about its rotation axis, the sample carrier 3 is oriented such that a counterpart fixing means 25, which is shown here as a notch for form-fit interaction or can be provided an an electrically, optically, magnetically or generally machine-readable marking, is oriented opposite the ball pin 21 or generally the first fixing means 14. This orientation allows the first fixing means 14 to engage in the counterpart fixing means 25 when the lowering movement 15 is performed. In this case, the sample carrier 3 is moved in a first lowering movement 15 initially along the rotation axis 5 until the first fixing means 14 contacts the sample carrier 3. Alternatively, the first lowering movement 15 is configured as a relative movement between the sample carrier 3 and the adjusting and measuring unit 6, wherein the adjusting and measuring unit 6 can be moved for example toward a stationary sample carrier 3.

After completion of the first lowering movement 15, the situation shown in FIG. 3 thus arises, in which the sample carrier 3, on account of the shape of the counterpart coupling element 25, has been rotated automatically about the rotation axis 5 until the first fixing means 14 latches onto the sample carrier 3. In this way, the position of the cytometer channel 12 is defined in the first adjustment direction 16.

The sample carrier 3 is then moved in a second lowering movement 17, in which the position of the cytometer channel 12 is defined in a second adjustment direction 18 along the optical path 11. The second lowering movement 17 is in this case performed until a second fixing means 19 contacts the sample carrier 3. Alternatively, the second lowering movement 17 can also be effected as a relative movement, for example by means of the adjusting and measuring unit 6 being moved toward the sample carrier 3.

The first fixing means 14 and the second fixing means 19 contact the underside 20 of the sample carrier 3. The first fixing means 14 and the second fixing means 19 are each oriented such that the sample carrier 3 is contacted axially during the lowering movements 15 and 17.

To support the second lowering movement 17 and, if appropriate, also the first lowering movement 15, a holding-down device 21 is provided, which acts on the sample carrier 3. Here, the holding-down device 21 engages on the side 22 facing away from the underside 20, i.e. the upper face of the sample carrier 3. To simplify matters, the holding-down device 21 has been omitted in FIGS. 1, 5 and 6. It will be seen from FIGS. 2 to 4 that the holding-down device 21 is arranged in the continuation or alignment of the optical path 11. This results in the pressing forces from the fixing means 14 and 19 being received centrally on the opposite side of the sample carrier 3.

The first fixing means 14 is designed as a ball pin 23. The ball pin 23 is, in a manner known per se, a tip which is directed toward the sample carrier 3 and which has a hemispherical shape in order to slide easily on the sample carrier 3.

The second fixing means 19 also has a ball pin 24.

A counterpart fixing means 25 is formed on the underside 20 of the here disk-shaped sample carrier 3, which counterpart fixing means 25 interacts with the first fixing means 14 for definition of the orientation of the cytometer channel 12 transverse to its direction of extent and transverse to the optical path 11.

On the rotatable and here disk-shaped sample carrier 3, the counterpart fixing means 25 is formed as a wedge-shaped recess, which extends radially with respect to the rotation axis 5.

In the defined position of the cytometer channel 12, the ball pin 23 of the first fixing means 14 latches into this counterpart fixing means 25, as is shown in FIG. 3.

A ball latch is thus formed.

The hemispherical tips of the ball pins 23 and 24 each define a bearing point on the sample carrier 3. The optical path 11 extends between the ball pin 23 as part of the first fixing means 14 and the ball pin 24 as part of the second fixing means 19. The optical path 11 here intersects a connection line between the stated bearing points of the ball pin 23 and of the ball pin 24.

The second fixing means 19 has a further ball pin 26, which likewise defines a bearing point on the sample carrier 3.

The fixing means 14, 19 are arranged at a distance from the rotation axis 5, such that the stated bearing points are spaced apart from each other and spaced apart from the rotation axis 5. The ball pins 24, 26 are likewise arranged such that a connection line between the associated bearing points is intersected by the optical path 11.

The ball pin 23 is acted upon by a spring element 27, such that the first fixing means 14 is elastically resilient in a direction along the optical path 11. This has the effect that, in the situation according to FIG. 4, the ball pin 23 is able to engage in the counterpart fixing means 25 without this giving rise to an overdetermined situation.

From what is described above, it will be clear that the first adjustment direction 16 is oriented transversely with respect to a radial direction in relation to the rotation axis 5, i.e. oriented in the circumferential direction or tangentially, whereas the second adjustment direction 18 is oriented transversely with respect to the first adjustment direction 16 and axially in relation to the rotation axis 5.

FIGS. 5 and 6 show that the second fixing means 19 is arranged at a distance from the rotation axis 5. The ball pins 24 and 26 are here arranged at a matching distance from the rotation axis 5.

This has the effect that, when the rotation unit 4 is lowered in the second lowering direction 17, and after the sample carrier 3 has been contacted by the ball pins 24 and 26, the sample carrier 3 is pivoted about a connection line of the bearing points of the ball pins 24 and 26 if a clearance of the rotation unit 4 so permits. The rotation unit 4 thus forms a bearing point with play for the sample carrier 3.

However, this pivoting movement does not lead to a new orientation of that part of the cytometer channel 12 containing the point of intersection with the stated connection line. Since the stated connection line, the cytometer channel 12 and the optical path 11 intersect at this point, the pivoting does not change the relative position of the point of intersection in relation to the cytometer channel 12 and the optical path 11. Although the sample carrier 3 is thus not clearly defined, apart from the play of the rotation unit 4, i.e. apart from a tolerance of the bearing point, this is nevertheless sufficient for the purposes of the cytometric measurement, since the remaining degree of freedom is not relevant as regards a precise orientation of the cytometer channel 12 on the optical path 11.

Figure 1:
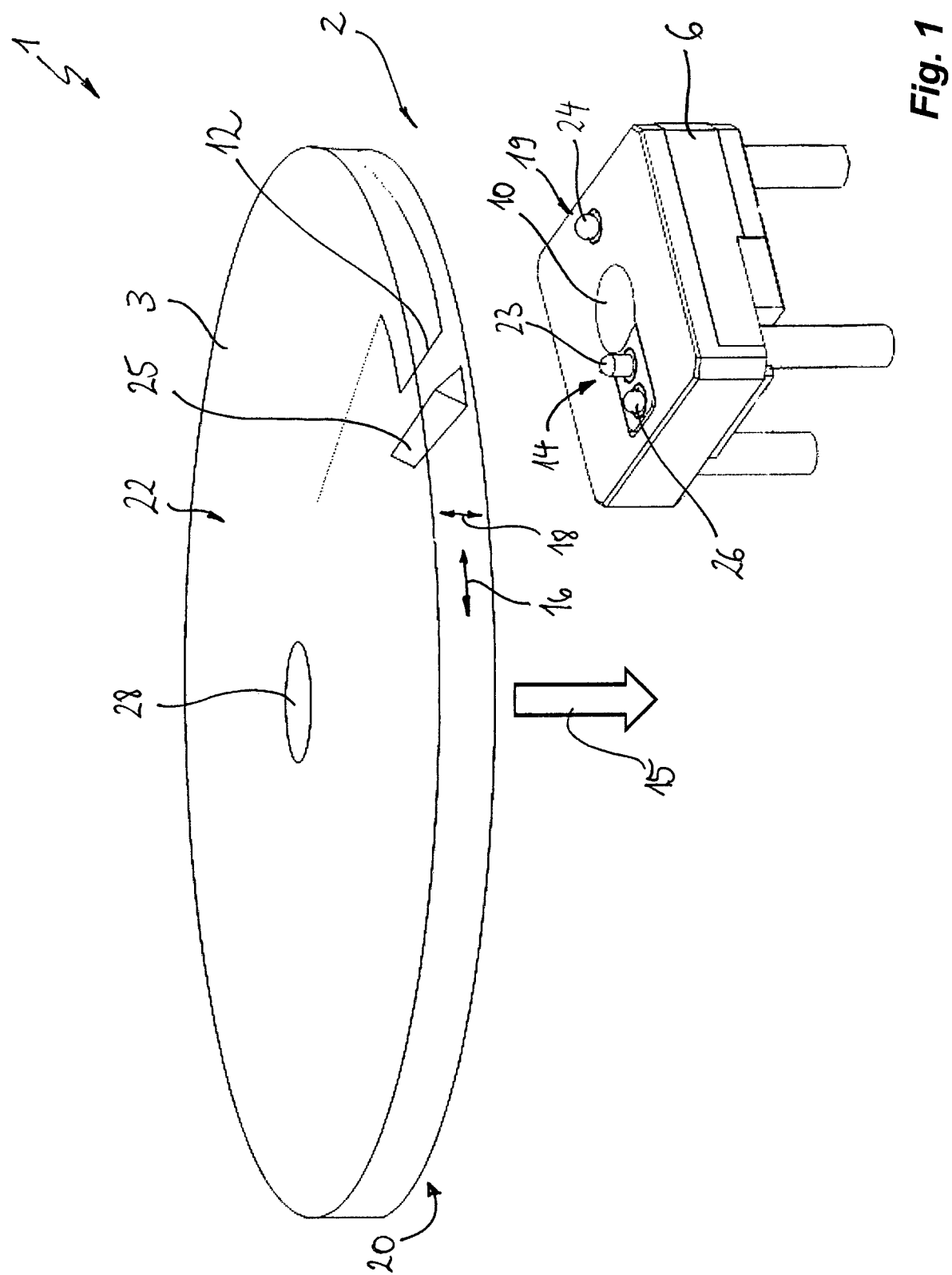
FIG. 1 shows a three-dimensional oblique view of a cytometer unit according to the invention with an insertable sample carrier.

The sample carrier 3 has a coupling site 28, which is shown in FIGS. 1, 5 and 6. With the coupling site 28, the rotatable sample carrier 3 can be coupled onto the rotation unit 4.

The coupling site 28 thus likewise defines the position of the rotation axis 5 on the sample carrier 3 in the position of use of the latter.

The stated directional specifications "axial", "radial" and "tangential" can thus likewise refer to the coupling site 28.

It will be seen from FIG. 1 that the cytometer channel 12 is oriented radially with respect to this rotation axis 5. Thus, the sample carrier 3 can be used in the cytometer unit 1 to carry out the method according to the invention.

In the method according to the invention, the sample carrier 3, in which the cytometer channel 12 contains a sample to be tested, is brought into the optical path 11. The sample carrier 3 is in this case mounted rotatably about the rotation axis 5 and is contacted by the first fixing means 14, at a distance from the optical path 11 and from the rotation axis 5, in such a way that a position of the cytometer channel 12 in the first adjustment direction 16 is defined relative to the optical path 11. For this purpose, the sample carrier 3 is rotated about the rotation axis 5.

Thereafter, or at the same time, the sample carrier 3 is contacted by a second fixing means 19, which has two ball pins 24 and 26 in this case, in order to fix the orientation of the cytometer channel 12 with respect to the optical path 11. Thus, the position of the cytometer channel 12 along the optical path 11 is defined by the second fixing means. In the definition of the position of the cytometer channel 12 in the first adjustment direction 16, the ball latch 23 of the first fixing means 14 interacts with the counterpart fixing means 25 in the manner of a ball latch. The rotation movement of the sample carrier 3 is thus carried out until the ball pin 23 is latched in the counterpart fixing means 25.

After the orientation has been defined, the cytometric measurement is carried out with the sample carrier 3 stationary.

In the cytometer unit 1 with a receptacle 2 into which a rotatable and preferably disk-shaped sample carrier 3 is insertable, it is proposed that a first fixing means is defined for the definition of a position of a cytometer channel 12 of the inserted sample carrier 3 transverse to its direction of extent and transverse to an optical path 11 with which a cytometric measurement can be carried out and to use a second fixing means 19 to define a position of the cytometer channel 12 of the inserted sample carrier 3 along the optical path 11.

LIST OF REFERENCE SIGNS 1 cytometer unit
2 receptacle
3 sample carrier
4 rotation unit
5 rotation axis
6 adjusting and measuring unit
7 laser light source
8 light beam
9 mirror
10 lens
11 optical path
12 cytometer channel
13 detector
14 first fixing means
15 first lowering movement
16 first adjustment direction
17 second lowering movement
18 second adjustment device
19 second fixing means
20 underside
21 holding-down device
22 facing-away side
23 ball pin
24 ball pin
25 counterpart fixing means
26 ball pin
27 spring element
28 coupling site

I claim:

1. A cytometer unit (1) comprising a receptacle (2) for an insertable and rotatable sample carrier (3), a rotation unit (4) that is couplable to an inserted sample carrier (3), and with which the sample carrier (3) inserted into the receptacle (2) is rotatable, arranged in the receptacle (2), and an optical path (11) for carrying out a cytometric measurement on a cytometer channel (12) of the inserted sample carrier (3) formed in the receptacle (2), a first fixing device (14) that contacts the inserted sample carrier (3) such that a position of the cytometer channel (12) is defined in a first adjustment direction (16) transversely with respect to the optical path (11), and a second fixing device (19) that contacts the inserted sample carrier (3) such that a position of the cytometer channel (12) is defined in a second adjustment direction (18) along the optical path (11) in a position contacting the inserted sample carrier (3).

2. The cytometer unit (1) as claimed in claim 1, wherein at least one of the first fixing device (14) or the second fixing device (19) contact the sample carrier (3) on one side, and a holding-down device (21) contacts the inserted sample carrier (3) from a side facing away from the at least one of the first fixing device (14) or the second fixing device (19).

3. The cytometer unit (1) as claimed in claim 1, wherein the first fixing device (14) interacts with form-fit engagement with a counterpart fixing device (25) on the sample carrier (3).

4. The cytometer unit (1) as claimed in claim 1, wherein the optical path (11) is formed between at least one part of the first fixing device (14) and at least one part of the second fixing device (19).

5. The cytometer unit (1) as claimed in claim 1, wherein at least one of the first fixing device (14) or the second fixing device (19), for defining the position in the second adjustment direction (18), for two bearing points for the insertable sample carrier (3), and the optical path (11) intersects a connection line between the two bearing points.

6. The cytometer unit (1) as claimed in claim 1, wherein at least one of the first adjustment direction (16), in relation to a rotation axis (5) of the rotation unit (4), is oriented transversely with respect to a radial direction, the second adjustment direction (18), in relation to the rotation axis (5)

of the rotation unit (4), is oriented transversely with respect to the radial direction and a tangential direction.

7. A cytometry method comprising for a cytometric measurement, bringing a cytometer channel (12) formed in a rotatable sample carrier (3) and containing a sample to be tested into an optical path (11), rotatably mounting the sample carrier (3) about a rotation axis (5), by contacting the sample carrier (3) with a first fixing device (14) for an orientation of the cytometer channel (12) on the optical path (11) at a distance from the rotation axis (5) in such a way that a position of the cytometer channel (12) is defined in a first adjustment direction (16) transverse to the optical path (11), and contacting the sample carrier (3) by a second fixing device (19) for an orientation of the cytometer channel (12) on the optical path (11) at a distance from the rotation axis (5) in such a way that a position of the cytometer channel (12) is defined in a second adjustment direction (18) along the optical path (11).

8. The cytometry method as claimed in claim 7, wherein the sample carrier (3) is contacted by at least one of the first fixing device (14) or the second fixing device (19) on one side.

9. The cytometry method as claimed in claim 7, further comprising bringing the first fixing device (14) and a counterpart fixing device (25) of the sample carrier (3) into engagement with each other in order to fix the sample carrier (3) with a form fit for the definition of the position of the cytometer channel (12) in the first adjustment direction (16).

10. The cytometry method as claimed in claim 7, further comprising at least one of rotating the sample carrier (3) about the rotation axis (5) for the definition of the position in the first adjustment direction (16), or displacing the sample carrier (3) along the rotation axis (5) for the definition of the position in the second adjustment direction (18).

11. A combination of a rotatable sample carrier (3) and a cytometer unit (1), the rotatable sample carrier (3) comprising a cytometer channel (12), a coupling site (28) for a rotation unit (4), and a counterpart fixing device (25), wherein the counterpart fixing device (25) is configured for a form-fit fixing of the sample carrier (3) transversely with respect to a direction of extent of the cytometer channel (12); and the cytometer unit comprising a receptacle for the sample carrier and a rotation unit that is coupled to the inserted sample carrier and with which the sample carrier (3) inserted into the receptacle (2) is rotatable, and an optical path (11) for carrying out a cytometric measurement on a cytometer channel (12) of the inserted sample carrier (3) formed in the receptacle (2), a first fixing device (14) that contacts the inserted sample carrier (3) such that a position of the cytometer channel (12) is defined in a first adjustment direction (16) transversely with respect to the optical path (11), and a second fixing device (19) that contacts the inserted sample carrier (3) such that a position of the cytometer channel (12) is defined in a second adjustment direction (18) along the optical path (11) in a position contacting the inserted sample carrier (3).

12. The cytometer unit as claimed in claim 1, wherein at least one of the first fixing device (14) or the second fixing device (19) are designed as at least one ball pin (23, 24, 26).

13. The cytometer unit as claimed in claim 3, wherein the first fixing device and the counterpart fixing device form a ball latch.

14. The cytometer unit as claimed in claim 1, wherein the first fixing device is adapted to yield elastically in a direction along the optical path.

15. The cytometry method as claimed in claim 8, wherein the first fixing device yields during the definition of the position in the second adjustment direction.

16. The cytometry method as claimed in claim 7, further comprising pivoting the sample carrier (3) about a connection line intersecting the optical path and extending between two bearing points defined by at least one of the first fixing device or the second fixing device.

* * * * *